United States Patent
Kuwabara

(10) Patent No.: US 6,324,251 B1
(45) Date of Patent: Nov. 27, 2001

(54) FLUORESCENT X-RAY ANALYZER INCLUDING DETECTION SIGNAL CORRECTION BASED ON POSITION VARIATION

(75) Inventor: Shoji Kuwabara, Osaka (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 09/464,585

(22) Filed: Dec. 16, 1999

(30) Foreign Application Priority Data

Dec. 25, 1998 (JP) ................................... 10-370930

(51) Int. Cl.[7] ................................. G01N 23/223

(52) U.S. Cl. ............................... 378/48; 378/44; 378/207

(58) Field of Search .................. 378/48, 44, 45, 378/207

(56) References Cited

U.S. PATENT DOCUMENTS

| | | | | |
|---|---|---|---|---|
| 4,797,906 | * | 1/1989 | Smith | 378/44 |
| 5,062,127 | * | 10/1991 | Sayama et al. | 378/48 |
| 5,457,726 | * | 10/1995 | Miyazaki | 378/48 |

* cited by examiner

*Primary Examiner*—Drew Dunn
(74) *Attorney, Agent, or Firm*—Coudert Brothers

(57) ABSTRACT

A fluorescent x-ray analyzer has a sample table with a movable part such as a turret which can be moved such that a sample which is placed at a specified sample position thereon can be moved to a specified position for analysis, an x-ray source for emitting primary x-rays, a detector for detecting secondary x-rays emitted from the irradiated sample, and a correcting device for correcting the detection signal outputted from the detector for an error caused by the variation in the sample position, or the variations in the distance between the plane of measurement and the x-ray source and/or the detector.

12 Claims, 2 Drawing Sheets

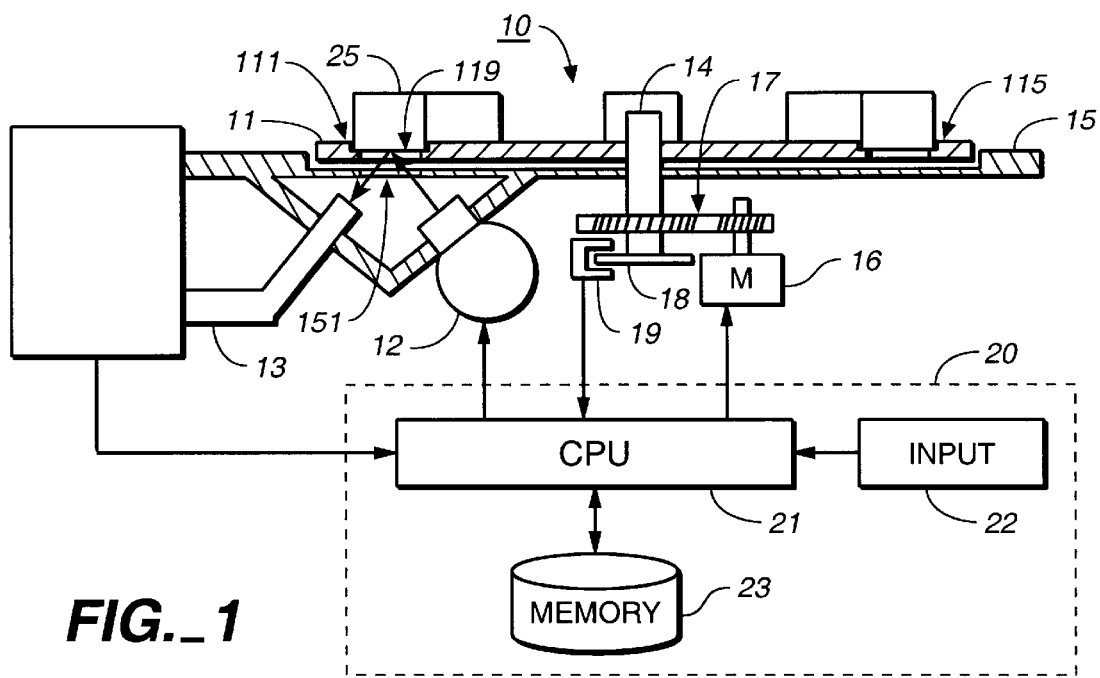
FIG._1
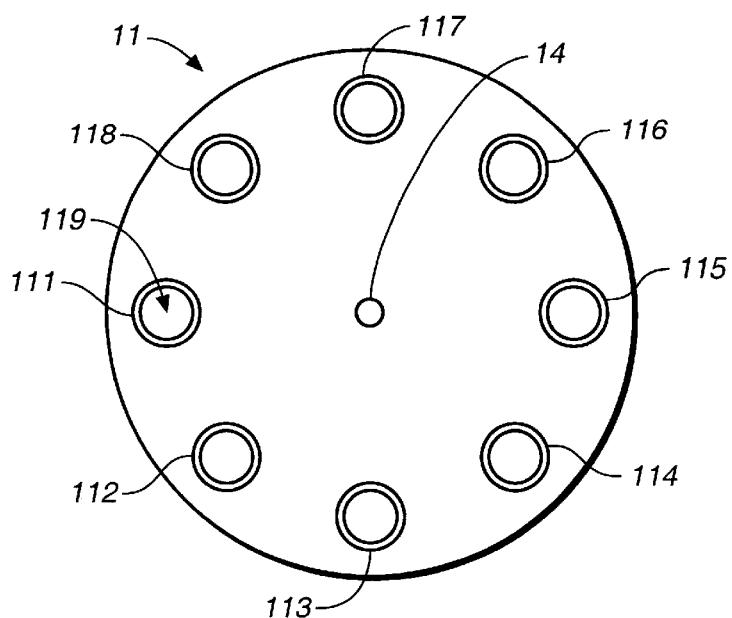
FIG._2

| IDENTIFIER | P1 | P2 | P3 | P4 | P5 | P6 | P7 | P8 |
|---|---|---|---|---|---|---|---|---|
| RATIO | 1.000 | 0.998 | 0.999 | 1.001 | 1.002 | 0.999 | 0.998 | 0.999 |
FIG._3
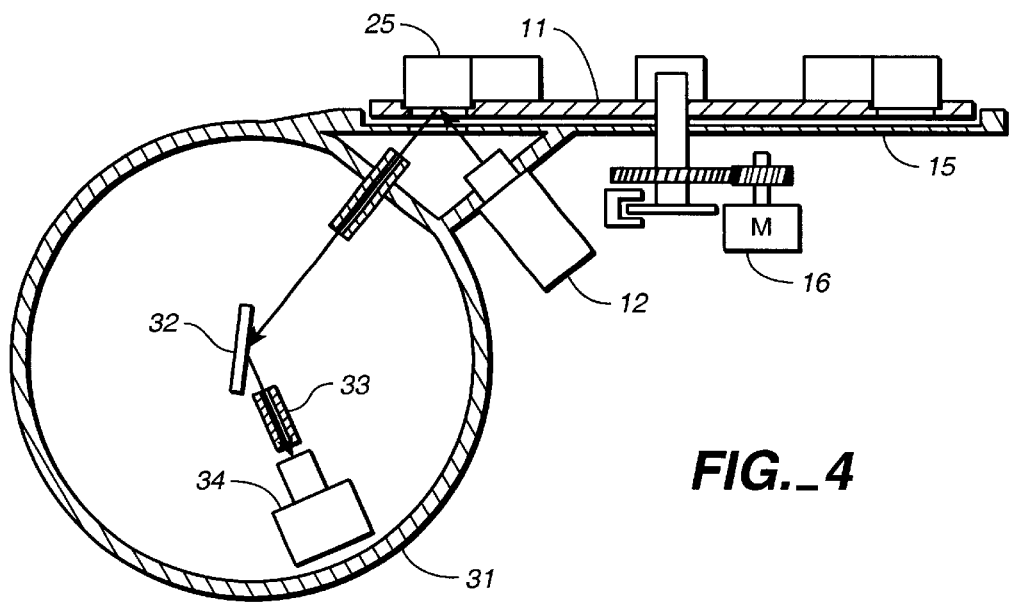
FIG._4
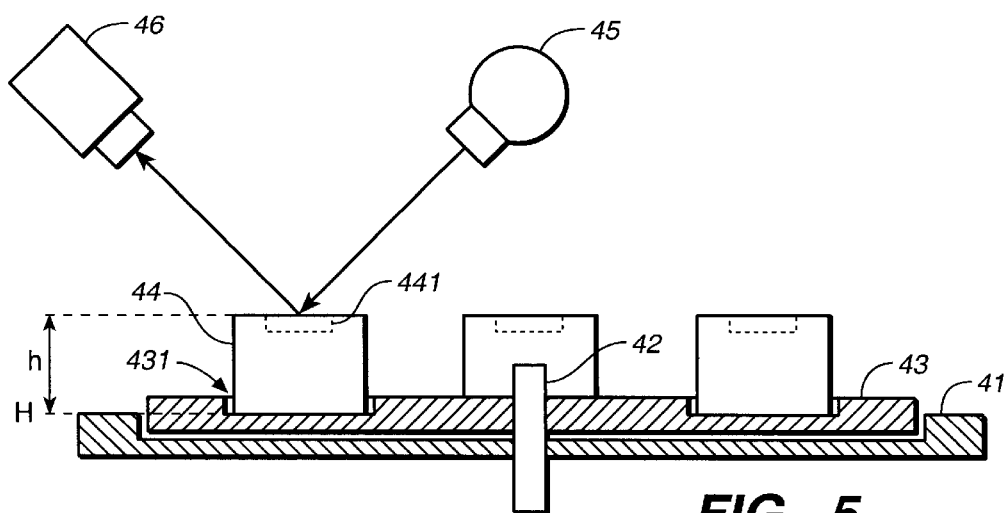
FIG._5

FLUORESCENT X-RAY ANALYZER INCLUDING DETECTION SIGNAL CORRECTION BASED ON POSITION VARIATION

BACKGROUND OF THE INVENTION

This invention relates to a fluorescent x-ray analyzer.

A fluorescent x-ray analyzer of a so-called bottom lighting type is characterized as having an x-ray source disposed below a sample table for supporting a sample thereon such that the primary x-ray emitted from the source will be made incident onto an opening at a specified position on the sample table. If a sample is placed at this specified position and the primary x-ray beam from the source is made incident thereon through the opening, a secondary x-ray beam is generated on the lower surface of the sample and this secondary x-ray beam is analyzed by means of a detector such as a semiconductor detector to obtain measured data.

Some of such fluorescent analyzers are equipped with a sample table capable of not only carrying thereon a plurality of samples to be analyzed but also transporting a selected one of them to a specified position for analysis. A typical example of sample table of this kind comprises a rotatable disk-shaped member referred to as a turret, having a plurality of openings at equal distances from the center of this disk Each of the openings has a sample position associated therewith such that the turret is rotated a sample is selected.

With a fluorescent x-ray analyzer provided with a turret structured as above, the height of the target surface to be measured will generally change with respect to a reference surface, depending on which of the sample positions is disposed at the position for measurement. If this height changes, both the path length of the primary x-ray beam from the source to the bottom surface of the sample and that of the secondary beam from the bottom surface of the sample to the detector will also change. A change in the path length of the primary beam means that the intensity of the primary x-ray beam changes on the bottom surface of the sample and hence that the intensity of the secondary beam will change accordingly. A change in the path length of the secondary beam means that its intensity is not constant as it is received by the detector. In other words, even if primary beams of the same intensity are used to analyze the same sample, there will be variations in the signals outputted from the detector, depending on the position of the sample placed on the turret. For this reason, it has been a common practice in the production of a turret to minimize the differences among the heights of the sample positions.

This may be done, for example, by using primary beams of the same intensity and the same sample to measure the intensities of the signals outputted from the detector as the sample is moved from one sample position to another. If the error is expressed in terms of the ratio between the amplitude of the variations and the average signal intensity, an error as small as about 0.02–0.3% is usually required for a fluorescent x-ray analyzer of a medium capability. In order to reduce the error to this level the differences in height at different sample positions must be within a range of several to several tens in units of $\mu$m. Thus, it has been necessary to use not only an expensive high-precision machine for the production of a sample table with a turret but also a micro-gauge or the like to assemble the produced parts with a high degree of accuracy. It now goes without saying that the use of such apparatus adds to the production cost.

It should be appreciated that a problem of this kind is not unique to fluorescent x-ray analyzers but may well come about with fluorescent x-ray analyzers of different types. In the case of a fluorescent x-ray analyzer with a so-called X-Y stage or an r$\theta$ stage adapted to two-dimensionally move the sample position with respect to the x-ray source, the distance between the x-ray source and the target surface for the measurement is likely to vary, depending on the position at which the sample is placed.

SUMMARY OF THE INVENTION

It is therefore an object of this invention in view of the problems described above to provide a fluorescent x-ray analyzer capable of always yielding a correct result of measurement even if the distance between the x-ray source and the target surface of a sample to be measured may change as the sample to be measured is switched or the position of the sample is changed.

A fluorescent x-ray analyzer embodying this invention, with which the above and other objects can be accomplished, may be characterized as comprising a sample table having a movable part, positioning means for moving this movable part such that a sample which is placed at a specified sample position on the movable part of the sample table is at a specified position where it is to be analyzed, an x-ray source for emitting primary x-rays to a specified target measurement plane of the sample, a detector for detecting secondary x-rays emitted from the irradiated sample, and correcting means for correcting the detection signal outputted from the detector for an error caused by the variation in the sample position, or the variations in the distance between the plane of measurement and the x-ray source and/or the detector.

In the description given above, what is referred to as the movable part of the sample table may be a turret of which the position may be specified by an angle, an X-Y stage of which the position may be specified by an X-coordinate and a Y-coordinate, or an r$\theta$ stage of which the position may be specified by a radial direction and an angular orientation. With a fluorescent x-ray analyzer provided with a movable part of this type, the distance between the plane of measurement on which the sample is analyzed and the x-ray tube and/or the detector will change, depending on the position of the movable part. According to this invention, such variations due to the positioning of the movable part of the sample table is compensated for, or corrected, according to a preliminarily measured characteristics of the sample positions.

When the analyzer is adjusted, the following measurements are carried out preliminarily to its actual operation by placing a standard sample at each of the plurality of sample positions on the movable part of the sample table. The standard sample may be copper or iron with a sufficient high degree of purity having a high rate of emission of secondary x-rays. For each sample at each sample position, the movable part of the sample table such as a turret is transported to the position for irradiating it with the primary x-rays from an x-ray source, and the corresponding output signal from the detector is analyzed by converting it by means of an analog-to-digital convertor in a well-known manner, obtaining information representing the intensity of this output signal. The intensity data thus obtained from the samples at different sample positions are collected and stored in correlation with the individual sample positions in the form of a correction table. What is stored in the form of a correction table, however, need not be the measured intensity values but may be, for example, their ratios with respect to a selected one of them.

When the analyzer is used thereafter in an actual analysis, such a correction table is conveniently utilized as a database for the correction of actually measured data. Thus, although the components of the sample table is not built or assembled with a sufficient accuracy and there may be variations among the sample positions in the distances between the sample and the x-ray source and/or the detector, such variations are efficiently compensated for by using the data in the correction table stored in the memory device.

BRIEF DESCRIPTION OF THE DRAWINGS

The accompanying drawings, which are incorporated in and form a part o this specification, illustrate embodiments of the invention and, together with the description, serve to explain the principles of the invention. In the drawings:

FIG. 1 is a combination of a schematic sectional view and a block diagram of a fluorescent x-ray analyzer embodying this invention;

FIG. 2 is a plan view of the turret shown in FIG. 1;

FIG. 3 is an example of correction table which is stored in the memory device shown in FIG. 1;

FIG. 4 is a schematic sectional view of another fluorescent x-ray analyzer of the wavelength-dispersion type; and FIG. 5 is a schematic sectional view of a portion of still another fluorescent x-ray analyzer of the type irradiating a sample from above.

DETAILED DESCRIPTION OF THE INVENTION

The invention is described next by way of an example. FIG. 1 shows a fluorescent x-ray analyzer 10 embodying this invention having a turret 11 adapted to carry thereon a plurality of solid samples 25. It further includes an x-ray tube 12 for generating primary x-rays, a detector 13 (such as a semiconductor detector or a proportional counter tube) for detecting the secondary x-rays generated by the sample, a sample table 15 provided with a rotary shaft 14 for supporting the turret 11 and an opening 151 for allowing x-rays to pass through, a motor 16 and a gear mechanism 17 for rotating the rotary shaft 14, and a rotary plate 18 with a slit and a transmission type optical sensor 19 for detecting the angular position of the turret 11. The x-ray tube 12, the detector 13, the motor 16 and the transmission type optical sensor 19 are connected to a control device 20 comprising a computer. The control device 20 is provided with a central processing unit (CPU) 21 for controlling the operations of the various components and processing the data of all kinds obtained by measurements, an input device 22 (such as a keyboard or a mouse) through which a user can input various commands to the CPU 21 and a memory device 23 such as a hard disk for storing data to be used for measurements as well as data obtained by the measurements.

As shown in FIG. 2, the turret 11 is provided with eight circular indentations 111–118 serving as sites for receiving solid samples 25 therein. These indentations 111–118 are at a same distance from the rotary shaft 14. Each indentation has an opening at its bottom for allowing x-rays to pass therethrough. Numeral 119, for example, indicates an opening at the bottom of the indentation 111.

FIG. 3 shows an example of correction table stored in the memory device 23 for showing the relationship between identifiers P1–P8 for indicating the positions of the indentations 111–118 and the intensity ratios R1–R8 corresponding thereto. The values of the intensity ratios R1–R8 may be determined as follows, for example, at the time of adjustment of the apparatus.

For this purpose, solid samples 25 each holding one of mutually identical standard samples are prepared, and the user places one in each of the indentations 111–118. The input device 22 is then operated to transmit to the CPU 21 a command to prepare a correction table. When this command is received, the CPU 21 responds by controlling the operation of the motor 16 while making reference to the output signals from the optical sensor 19 such that the first indentation 111 on the turret 11 will come to the measurement position directly above the opening 151 in the sample table 15. Thereafter, the CPU 21 causes the x-ray tube 12 to emit a primary x-ray beam of specified intensity for specified length of time and measures the intensity of the corresponding signal outputted from the detector 13. The measured intensity I1 thus detected is stored in a memory (not shown) in correlation with the position identifier P1 associated with the indentation 111. After the measurement on the standard sample in the indentation 111 is thus completed, the same routine is repeated for the standard samples in the other indentations 112–118, obtaining each time the intensity I1-I8 from the detector 13, and the CPU 21 stores these data in correlation with the identifiers P2-P8.

After the intensity values I1-I8 are thus obtained, the value I1 is used as the reference intensity I0 and the ratios Ri (i=2–8) of the other intensity values I2-I8 to this reference intensity I0 are calculated as intensity ratios Ri=Ii/I0. The values of these intensity ratios are then stored in the memory device 23 in correlation with the identifiers Pi as shown in FIG. 3.

In the case of an actual measurement, the correction table thus prepared is used as follows to correct the intensity of signals outputted from the detector 13.

Let us assume that the detector 13 has outputted a signal with intensity I after receiving secondary x-rays generated from a certain sample. Thereupon, the CPU 21 ascertains the identifier Pi of the indentation at the measurement position of the sample table 15 when the signal was outputted and reads out the intensity ratio Ri corresponding to this identifier Pi from the correction table stored in the memory device 23. The corrected intensity value I' is obtained by dividing the outputted intensity I by the intensity ratio Ri which has been read out, or I'=I/Ri.

Although the invention was described above by way of only one example, this example is not intended to limit the scope of the invention. Many modifications and variations are possible within the scope of the invention. For example, the correction table need not be for showing the relationship between the identifiers Pi and the intensity ratios Ri. The correlation table may be for showing the relationship between the identifiers Pi and the inverses of the intensity ratios Ri, or the relationship between Pi and 1/Ri. If such a correction table is stored, the correct intensity value I' is obtained from the measured intensity I by retrieving the value of the inverse of the intensity ratio of the corresponding identifier and multiplying the value of this inverse with the measured intensity, that is, I'=I×(1/Ri). As still another example, the correction table may store the actually measured intensity values rather than intensity ratios with respect to one of the measured intensity values. In such a case, the corrected intensity value will be obtained by the formula I'=I/(Ii×I0).

In order to prepare the correction table, it is not always necessary to irradiate standard samples placed at all sample positions with x-rays of the same intensity, as described above. A correction table may be equally practically prepared by measuring the distance between the x-ray tube 12 and the measurement plane, the distance between the detector 13 and the measurement plane, the angle of incidence for the primary x-ray beam onto the measurement plane, the angle of emission of the secondary beam from the measurement plane, etc. for each sample position and obtaining the values of the intensity ratios Ri theoretically from these measured values.

Although the invention was described above by way of an example having a turret with eight sample positions (in the form of indentations), a common practice is to provide a fluorescent x-ray analyzer with a plurality of turrets and to use a selected one of them, depending on conditions such as the shape, size or state (that is, whether it is liquid, solid or powder) of the samples. In such applications, there may also be provided a means for specifying the type of turret to be used and also a memory device for storing a turret database containing various data related to the selection of turrets such as the number of sample positions on each of the available turrets and the relationship between the position identifiers of its sample positions and the corresponding sensor outputs. When such a fluorescent x-ray analyzer is adjusted, a correction table is prepared as described above for each of the plurality of turrets and the prepared correction tables are stored in the memory device. In this manner, even when turrets are exchanged and the distance between the measurement plane of the sample 25 and the x-ray tube 12 or the detector 13 may change, the user has only to refer to a different correction table already stored in the memory device in order to reliably correct the output signals from the detector 13. Examples of means for specifying a turret include a display device capable of making on its screen a display, allowing the user to make a selection thereon by operating the input device 22. The CPU 21 may further be programed such that, when the user has thus specified one of the available turrets mentioned on the display screen, the data related to this selected turret will then be stored in a memory device (not shown).

The use of a turret is not an essential requirement of this invention. Since turrets are for the convenience of analyzing a plurality of samples sequentially, there is no need for a turret when there is only one sample to be analyzed. In view of such an event, the sample table 15 may be structured such that the turret 11 can be removed and a sample board supporting only one sample thereon may be affixed thereto. Such a sample board, however, may be considered a turret of a special kind having only one sample position and hence only one position identifier. Thus, the same procedure as described above may be followed at the time of each adjustment to prepare a correction table and to store the correction data in the memory device 23 such that output signals from the detector 13 can be properly corrected.

Although a rotary plate 18 with a slit and a transmission type optical sensor 19 were disclosed above with reference to FIG. 1 as means for detecting the angular position of the turret 11, neither is this intended to limit the scope of the invention. If the motor 16 is a pulse motor, for example, the angular position of the turret 11 can be controlled by the number of pulses given to such a pulse motor.

Although a semiconductor detector and a proportional counter tube were mentioned above as examples of detector for detecting the secondary x-rays generated by a sample, the present invention is applicable also to fluorescent x-ray analyzers of types other than the so-called energy-dispersing or non-dispersing type. FIG. 4 shows a fluorescent x-ray analyzer of the so-called wavelength-dispersing type adapted to disperse the secondary x-rays in the direction of the wavelengths by means of a light disperser 32 disposed inside a detection chamber 31, to select only a portion of the dispersed light corresponding to a specified wavelength by means of a slit 33 and to detect the selected portion by means of a detector 34. It now goes without saying that the present invention applies equally well to a fluorescent x-ray analyzer of this type.

FIG. 5 shows a fluorescent x-ray analyzer of still another type characterized as irradiating a sample from above. Explained briefly, such an analyzer may comprise a sample table 41 rotatably supporting a rotary shaft 42 driven by a motor (not shown) and a turret 43 which is attached to this rotary shaft 42 and is provided with a plurality of indentations 431 on its upper surface serving as sample positions. All of the indentations 431 have a same depth and sample holders 44 having the same height h are each placed inside a corresponding one of the indentations 431. Each holder 44 is formed with an indentation 441 on its upper surface for accepting a sample therein. When a sample is analyzed, the holder with the selected sample is disposed at the measurement position, the upper surface of the sample is exposed to the primary x-ray beam from above, and the secondary x-rays generated by the sample are detected by a detector 46. With a fluorescent x-ray analyzer of this type, the height H of the bottom surface of the indentation 431 is not always the same, and the sample holders 44 do not always have the same height h. As the turret 43 is rotated, the distances from the upper surface of the sample holder 44 to the x-ray tube 45 and to the detector 45 are expected to vary. Errors in the detection signals from the detector 45 due to such variations can also be corrected by a method embodying this invention.

What is claimed is:

1. A fluorescent x-ray analyzer comprising:

a sample table having a sample disposed at a sample position on said table;

an x-ray source for emitting primary x-rays to a target measurement plane of said sample;

a detector for detecting secondary x-rays emitted from said target measurement plane of said sample when irradiated by said primary x-rays; and correcting means for correcting an error in a detection signal outputted from said detector according to said sample position, said error being due to a variation in the position of said sample position with respect to said x-ray source and to said detector.

2. The fluorescent x-ray analyzer of claim 1 further comprising a memory device which stores information related to said variation preliminarily to an operation of said fluorescent x-ray analyzer, said correcting means correcting said error by retrieving said information from said memory device.

3. A fluorescent x-ray analyzer comprising:

a sample table having a movable part which can be moved to different table positions;

positioning means for moving said movable part of said sample table such that a sample placed at a sample position on said movable part of said sample table is at a specified measurement position;

an x-ray source for emitting primary x-rays to a target measurement plane of said sample;

a detector for detecting secondary x-rays emitted from said target measurement plane of said sample when irradiated by said primary x-rays; and correcting means for correcting an error in a detection signal outputted from said detector according to a variation in said sample position, said error being due to a variation in of said sample position with respect to said x-ray source and to said detector.

4. The fluorescent x-ray analyzer of claim 3 further comprising a memory device which stores information related to said variation preliminarily to an operation of said fluorescent x-ray analyzer, said correcting means correcting said error by retrieving said information from said memory device.

5. The fluorescent x-ray analyzer of claim 3 wherein said sample position is one of a plurality of sample positions which are all on said movable part of said sample table.

6. The fluorescent x-ray analyzer of claim 4 wherein said sample position is one of a plurality of sample positions which are all on said movable part of said sample table, and wherein said memory device preliminarily stores information related to variations in said plurality of sample positions, said correcting means correcting said error by identifying said one sample position and retrieving information related to said identified sample position to correct said error.

7. The fluorescent x-ray analyzer of claim 6 further comprising an input device, said information being inputted to and stored in said memory by an operator by operating on said input device.

8. The fluorescent x-ray analyzer of claim 3 wherein said movable part of said sample table is a turret which is rotatable around a shaft with respect to said sample table, said sample positions being at a same distance from said shaft.

9. The fluorescent x-ray analyzer of claim 4 wherein said movable part of said sample table is a turret which is rotatable around a shaft with respect to said sample table, said sample positions being at a same distance from said shaft.

10. The fluorescent x-ray analyzer of claim 5 wherein said movable part of said sample table is a turret which is rotatable around a shaft with respect to said sample table, said sample positions being at a same distance from said shaft.

11. The fluorescent x-ray analyzer of claim 6 wherein said movable part of said sample table is a turret which is rotatable around a shaft with respect to said sample table, said sample positions being at a same distance from said shaft.

12. The fluorescent x-ray analyzer of claim 7 wherein said movable part of said sample table is a turret which is rotatable around a shaft with respect to said sample table, said sample positions being at a same distance from said shaft.

* * * * *